US012778160B2

(12) United States Patent
Brashears et al.

(10) Patent No.: US 12,778,160 B2
(45) **Date of Patent: *Nov. 3, 2026**

(54) METHOD AND COMPOSITION FOR REDUCING PATHOGENS IN PET FOOD USING LACTIC ACID BACTERIA

(71) Applicant: Texas Tech University System, Lubbock, TX (US)

(72) Inventors: Mindy M. Brashears, Wolfforth, TX (US); David Campos, Muleshoe, TX (US); Kendra Nightingale, Lubbock, TX (US); Guy Loneragan, Wolfforth, TX (US); Markus F. Miller, Abernathy, TX (US)

(73) Assignee: Texas Tech University System, Lubbock, TX (US)

( * ) Notice: Subject to any disclaimer, the term of this patent is extended or adjusted under 35 U.S.C. 154(b) by 799 days.

This patent is subject to a terminal disclaimer.

(21) Appl. No.: 16/307,298

(22) PCT Filed: Jun. 28, 2017

(86) PCT No.: PCT/US2017/039661

§ 371 (c)(1),
(2) Date: Apr. 13, 2020

(87) PCT Pub. No.: WO2018/005599

PCT Pub. Date: Jan. 4, 2018

(65) Prior Publication Data

US 2020/0236968 A1 Jul. 30, 2020

Related U.S. Application Data

(60) Provisional application No. 62/355,379, filed on Jun. 28, 2016.

(51) Int. Cl.

| | |
|---|---|
| ***A23K 10/18*** | (2016.01) |
| ***A23K 30/00*** | (2016.01) |
| ***A23K 50/40*** | (2016.01) |
| ***C12N 1/20*** | (2026.01) |

(52) U.S. Cl.

CPC .............. *A23K 10/18* (2016.05); *A23K 30/00* (2016.05); *A23K 50/40* (2016.05); *C12N 1/20* (2013.01); *A23V 2400/181* (2023.08)

(58) Field of Classification Search

CPC ........ A23K 10/18; A23K 30/00; A23K 50/40; C12N 1/20; C12N 1/125

See application file for complete search history.

(56) References Cited

U.S. PATENT DOCUMENTS

| | | | | |
|---|---|---|---|---|
| 7,323,166 B2 * | 1/2008 | Brashears | C12N 1/205 | 435/252.3 |
| 8,496,925 B2 * | 7/2013 | Ware | A23B 4/22 | 424/93.4 |
| 8,771,675 B2 | 7/2014 | Zink et al. | | |
| 2004/0043012 A1 * | 3/2004 | Brashears | A23K 10/18 | 435/252.3 |
| 2011/0189132 A1 * | 8/2011 | Garner | A61K 35/66 | 424/93.3 |
| 2013/0011374 A1 | 1/2013 | Luquet et al. | | |

OTHER PUBLICATIONS

U.S. Appl. No. 16/310,981 (Year: 2018).*
U.S. Appl. No. 16/769,280 (Year: 2020).*
Castelli et al., "P3-38 Inhibition of Listeria monocytogenes with a Lactic Acid Bacteria Treatment for Fresh Strawberries", International Association for Food Protection, Wednesday, Aug. 6, 2014, (Year: 2014).*
Mao, "Molecular characterization of lacticins FS56 and FS92, two broad-spectrum bacteriocins produced by Lactococcus lactis strains" Purdue ePubs, https://docs.lib.purdue.edu/dissertations/AAI9951994/ (Year: 2005).*
Khodammohammadi, 2013, "Inhibition of Listeria monocytogenes in Ready to Eat Meals with Lactic Acid Bacteria", Master of Science, Texas Tech University, https://ttu-ir.tdl.org/server/api/core/bitstreams/a6d4df26-c425-42ea-b671-dbd40604807f/content (Year: 2013).*
Castillo, et al. "Novel Lactic Acid Bacteria (L 14 and L28) as a Biocontrol Agent for Inhibition of Salmonella in a Raw Chicken Fat Used as a Dog Food Ingredient" Mar. 29, 2016. [Retrieved from the Internet Sep. 20, 2017: <https://www.depts.ttu.edu/calue/docs/URC2016_Abstract_eBook.pdf>]; p. 25-26, Abstract 10, in entirety.
International Search Report, PCT/US17/39661 (ISA/US) Dec. 27, 2017.

* cited by examiner

*Primary Examiner* — Ruth A Davis
(74) *Attorney, Agent, or Firm* — Edwin S. Flores; Daniel J. Chalker; Chalker Flores, LLP

(57) ABSTRACT

The present invention provides a method for inhibiting the growth of pathogens in an animal feed comprising the steps of: contacting an animal feed with at least one lactic acid bacterium strain selected from the group consisting of *Lactobacillus salivarius* (L14, L28 and FS56), a mixture thereof; or a whey obtained from fermentation of the lactic acid bacterium strain, wherein the at least one lactic acid bacterium strain inhibits the growth of the pathogens, the nosocomial pathogens or the spoilage microorganisms in the pet food.

3 Claims, 6 Drawing Sheets

| | | | | | | | | | | | | | | | | | | | | | | | | | | |
|---|---|---|---|---|---|---|---|---|---|---|---|---|---|---|---|---|---|---|---|---|---|---|---|---|---|---|
| | 0 | 1 | 2 | 3 | 4 | 5 | 6 | 7 | 8 | 9 | P | P | P | P | 14 | 15 | P | 17 | P | P | 20 | 21 | P | 23 | 24 | 25 |
| | - | - | - | - | - | - | - | - | - | - | + | + | + | + | - | - | + | - | + | + | - | - | + | - | - | - |
| | - | - | - | - | - | - | - | - | - | - | + | + | + | + | - | - | + | - | + | + | - | - | + | - | - | - |
| | 0 | GLY | ERY | DARA | LARA | RIB | DXYL | LXYL | ADD | MDX | P | P | P | P | SBE | RHA | P | IND | P | P | MDM | MDG | P | AMY | ARB | ESC |

| FIG. 3A | FIG. 3B |
|---|---|

FROM FIG. 3A

METHOD AND COMPOSITION FOR REDUCING PATHOGENS IN PET FOOD USING LACTIC ACID BACTERIA

CROSS-REFERENCE TO RELATED APPLICATIONS

This application is the National Stage of International Application No. PCT/US2017/039661, filed on Jun. 28, 2017, which claims priority to U.S. Provisional Patent Application Ser. No. 62/355,379, filed on Jun. 28, 2016. The contents of both applications are incorporated by reference herein in their entirety.

TECHNICAL FIELD OF THE INVENTION

The present invention relates in general to the field of reducing pathogens in food products, specifically to compositions of matter and methods of making and using lactic acid bacterium for reducing pathogens in pet food.

BACKGROUND OF THE INVENTION

Without limiting the scope of the invention, its background is described in connection with reducing transmission of food borne illness in pet food.

The well-being of animals is closely related to their feeding. In addition to providing nutritional value, food composition influences the intestinal microflora equilibrium and may lead to or prevent gastrointestinal disorders. As meat-eaters, cats and dogs are characterized by a short digestive tract and a rapid flow rate of the bolus of food. Among the constituents of the gastrointestinal microflora of cats and dogs *Bacteroides* sp., *Clostridium* sp., Enterobacteriaceae, *Bifidobacterium* sp., *Lactobacillus* sp., *Streptococcus* sp., *Staphylococcus* sp. and yeasts can be recovered. The number and composition of this endogenous flora tend to be rather stable, although age and, to a lesser degree, food may modify it. Gastric acidity, bile, intestinal peristalsis and local immunity are factors thought to be important in the regulation of bacterial flora in the small intestine of various other mammals. Often canine and feline gastrointestinal disorders are linked to bacterial overgrowth and the production of enterotoxins produced by pathogenic bacteria. A common infection route relates to the ingestion of contaminated food, potentially leading to food-borne diseases. There is a clear need for new agents to control microorganisms either by reducing or inhibiting their growth. As a result, a great deal of effort has been expended in attempts to identify natural products that can be safely added for the purpose of inhibiting bacterial growth.

U.S. Pat. No. 8,771,675, entitled "Probiotic Strains for Pets" disclose novel strains of probiotics for use in the gastrointestinal tract of a pet. The probiotics are capable of fermenting starch to produce lactic acid and/or hydrogen peroxide anti-pathogenic metabolites.

U.S. Patent Application Publication No. 2013/0011374, entitled "Growth Inhibition of Microorganisms by Lactic Acid Bacteria," relates to growth inhibition of microorganisms by lactic acid bacteria; the reduction and/or treatment of food-borne pathogen infections and/or nosocomial infections; the inhibition of spoilage microorganisms in food products and the modulation of gut flora.

BRIEF SUMMARY OF THE INVENTION

The present invention provides a method for inhibiting the growth of pathogens in an animal feed comprising the steps of: contacting an animal feed with at least one lactic acid bacterium strain selected from the group consisting of *Lactobacillus salivarius* (L14—ATCC Deposit No. PTA-127732, L28—ATCC Deposit No. PTA-127731 and FS56—ATCC Deposit No. PTA-127730), a mixture thereof; or a whey obtained from fermentation of the lactic acid bacterium strain, wherein the at least one lactic acid bacterium strain inhibits the growth of the pathogens, the nosocomial pathogens or the spoilage microorganisms in the pet food.

The lactic acid bacterium strain may be admixed with the animal feed, or coated on the animal feed. The animal feed may be a cat food, dog food, horse food, cow food, chicken food, snake food, or other animal food. The animal feed may be a kibble, moist feed, or wet feed. The pathogens may be selected from the group consisting of *Staphylococcus aureus, Listeria innocua, Listeria monocytogenes, Enterococcus faecium* and *Enterococcus faecalis*. The pathogens may be selected from the group consisting of *Escherichia coli* and *Salmonella Typhimurium*. For example, the *Escherichia coli* comprises the O157:H7 serotype. The pathogens may be selected from the group consisting of *Aeromonas caviae; Aeromonas hydrophila; Aeromonas sobria; Bacillus cereus; Campylobacter jejuni; Citrobacter* ssp.; *Clostridium botulinum; Clostridium perfringens; Enterobacter* ssp.; *Enterococcus* ssp.; *Escherichia coli* enteroinvasive strains; *Escherichia coli* enteropathogenic strains; *Escherichia coli* enterotoxigenic strains; *Escherichia coli* O157:H7; *Klebsiella* ssp.; *Listeria monocytogenes; Plesiomonas shigelloides; Salmonella* ssp.; *Shigella* ssp.: *Staphylococcus aureus; Streptococcus* ssp.; *Vibrio cholerae; Yersinia enterocolitica*. More preferably, the pathogenic-bacteria are *Listeria monocytogenes*. The lactic acid bacterium strain may be *Lactobacillus salivarius* (L28) ATCC Deposit No. PTA-127731. At least one lactic acid bacterium strain is *Lactobacillus salivarius* (L28)) (ATCC Deposit No. PTA-127731), or strains MM13A, MM13B, P13, P17, Ecat, J19, J27, J35, J43, L14, L15, L17, L19, or L28.

A method for increasing the storage time of an animal feed by reducing the spoilage microorganisms comprising the steps of: combining an animal feed having one or more spoilage microorganisms with at least one lactic acid bacterium strain selected from the group consisting of *Lactobacillus salivarius* (L14—ATCC Deposit No. PTA-127732, L28—ATCC Deposit No. PTA-127731 and FS56—ATCC Deposit No. PTA-127730), a mixture thereof, or a whey obtained from fermentation of the lactic acid bacterium strain with the one or more spoilage microorganisms to reduce the number of one or more spoilage microorganisms in contact with the animal feed. The spoilage microorganisms may be selected from the group consisting of *Aeromonas caviae; Aeromonas hydrophila; Aeromonas sobria; Bacillus cereus; Campylobacter jejuni; Citrobacter* ssp.; *Clostridium botulinum; Clostridium perfringens; Enterobacter* ssp.; *Enterococcus* ssp.; *Escherichia coli* enteroinvasive strains; *Escherichia coli* enteropathogenic strains; *Escherichia coli* enterotoxigenic strains; *Escherichia coli O157*:H7; *Klebsiella* ssp.; *Listeria monocytogenes; Plesiomonas shigelloides; Salmonella* ssp.; *Shigella* ssp.: *Staphylococcus aureus; Streptococcus* ssp.; *Vibrio cholerae; Yersinia enterocolitica*. More preferably, the pathogenic-bacteria are *Listeria monocytogenes*. The lactic acid bacterium strain may be admixed with the animal feed, or coated on the animal feed. The animal feed may be a cat food, dog food, horse food, cow food, chicken food, snake food, or other animal food. The animal feed may be a kibble, moist feed, or wet feed. The lactic acid bacterium strain may be *Lactobacillus salivarius* (L28) At least one lactic acid bacterium strain is *Lactobacillus salivarius* (L28) (ATCC Deposit No. PTA-127731), or strains MM13A, MM13B, P13, P17, Ecat, J19, J27, J35, J43, L14, L15, L17, L19, or L28.

The present invention provides a method for reducing a pathogenic load in an animal feed comprising the steps of: mixing an animal feed having one or more pathogens with at least one lactic acid bacterium strain selected from the group consisting of *Lactobacillus salivarius* (L14—ATCC Deposit No. PTA-127732, L28—ATCC Deposit No. PTA-127731 and FS56—ATCC Deposit No. PTA-127730), a mixture thereof; or a whey obtained from fermentation of the lactic acid bacterium strain to reduce the pathogenic load.

The one or more pathogens may be selected from the group consisting of *Staphylococcus aureus, Listeria innocua, Listeria monocytogenes, Enterococcus faecium Enterococcus faecalis, Escherichia coli* and *Salmonella Typhimurium*. The pathogens may be selected from the group consisting of *Aeromonas caviae; Aeromonas hydrophila; Aeromonas sobria; Bacillus cereus; Campylobacter jejuni; Citrobacter* ssp.; *Clostridium botulinum; Clostridium perfringens; Enterobacter* ssp.; *Enterococcus* ssp.; *Escherichia coli* enteroinvasive strains; *Escherichia coli* enteropathogenic strains; *Escherichia coli* enterotoxigenic strains; *Escherichia coli* O157:H7; *Klebsiella* ssp.; *Listeria monocytogenes; Plesiomonas shigelloides; Salmonella* ssp.; *Shigella* ssp.: *Staphylococcus aureus; Streptococcus* ssp.; *Vibrio cholerae; Yersinia enterocolitica*. More preferably, the pathogenic-bacteria are *Listeria monocytogenes*. For example, the *Escherichia coli* may be the O157:H7 serotype. An animal feed product comprising an animal feed and at least one lactic acid bacterium strain selected from the group consisting of *Lactobacillus salivarius* (L14—ATCC Deposit No. PTA-127732, L28—ATCC Deposit No. PTA-127731 and FS56—ATCC Deposit No. PTA-127730), a mixture thereof; or a whey obtained from fermentation of the lactic acid bacterium strain.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
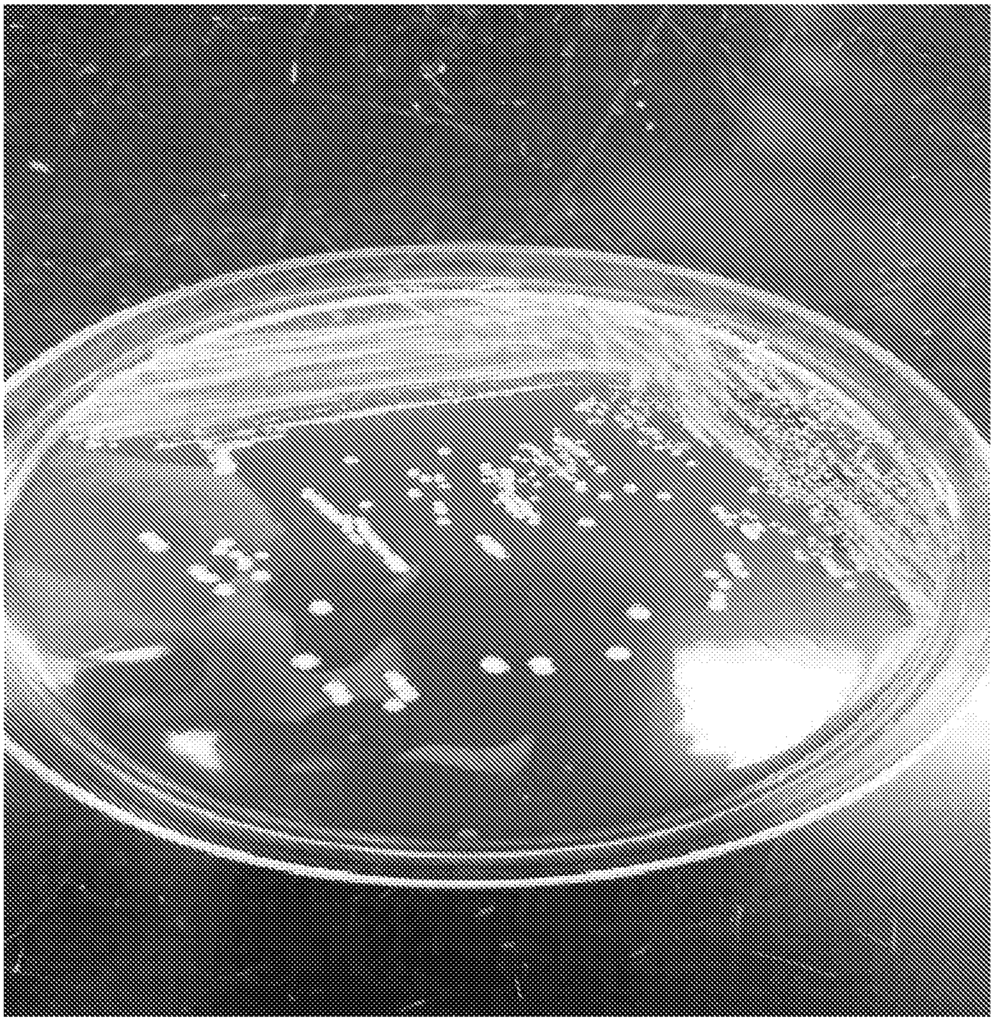
FIG. 1 shows the Lactic Acid Bacteriacolony morphology on MRS agar.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

The present invention provides compositions of matter and methods of making and using lactic acid bacterium for reducing pathogens in pet food and treats. The present invention uses lactic acid bacteria as additives to pet foods to inhibit food borne pathogens during both storage and production. The present invention uses one lactic acid bacterium strain is *Lactobacillus salivarius* (L28), or strains MM13A, MM13B, P13, P17, Ecat, J19, J27, J35, J43, L14, L15, L17, L19, or LP28.

The Veterinary Laboratory Investigation and Response Network (Vet-LIRN), Food Emergency Response Network (FERN), and the Microbiology Cooperative Agreement Program (MCAP) conducted a study to evaluate the prevalence of selected microbial organisms in various types of pet foods: Six laboratories analyzed approximately 1,056 samples over two years, testing for *Salmonella, Listeria, Escherichia coli* O157:H7, enterohemorrhagic *E. coli*, and Shiga toxin-producing strains of *E. coli* (STEC). Dry and semi-moist dog and cat foods purchased from local stores were tested. Raw dog and cat foods, exotic animal feed, and jerky-type treats purchased through the internet were tested in Phase 2. Of the 480 dry and semi-moist samples, only two tested positive: one for *Salmonella* and one for *Listeria greyii*. However, of the 576 samples analyzed during Phase 2, 66 samples were positive for *Listeria* (32 of those were *Listeria monocytogenes*) and 15 samples positive for *Salmonella*. These pathogens were isolated from raw foods and jerky-type treats, not the exotic animal dry feeds. This shows that raw pet foods may harbor food safety pathogens, such as *Listeria monocytogenes* and *Salmonella*. Consumers should handle these products carefully, being mindful of the potential risks to human and animal health. The disclosed invention utilizes the addition of lactic acid, specifically, a strain of *Lactobacillus salivarius* (L28) to reduce foodborne pathogens (i.e., *Salmonella* and *Listeria* spp.).

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The term "bacteriocidal effect" as used herein refers to any type of treatment, which effect the killing of bacteria (i.e. which reduce their numbers). This is in contrast to a "bacteriostatic effect" which refers to the situation where the treatment only inhibits the growth or reproduction of the bacteria. An agent is said to be a bactericide or a bacteriocide if the agent is able to kill one or more type of bacteria. A bacteriocide is said to possess bacteriocidal or bactericidal activity.

By "bacteriocins" we refer to peptides or protein molecules released extracellularly that are able to kill certain other closely related bacteria by a mechanism by which the producer cell exhibits a degree of specific immunity.

The term "dairy product" is intended to include any food product made using milk or milk products, including, but not limited to, milk, yogurt, ice cream, cheese, butter, and cream.

As used herein, the expression "effective amount" refers to the amount of the invention which gives rise to an inhibition of the bacterial growth or a reduction of the number of other bacteria from the food product.

The term "food product" and "food stuff" as used herein refers to any food that is susceptible to spoilage as a result of bacterial growth and proliferation, e.g., but not limited to, meat, dairy products, vegetables, fruits and grains.

As used herein, the term "meat" refers to any meat product or meat by-product (including those processed) from an animal which is consumed by humans or animals, including, without limitation, meat from bovine, ovine, porcine, poultry, fish and crustaceous seafood. As used in the present application, the term "ready to eat meat product", also referred to as RTE meat product, is intended to include any meat product which does not require cooking prior to consumption.

The terms "refrigerated product" or "preserved in a refrigerated state" are equally used and refer to food products which are stored at temperatures ranging from to 2 to 10° C. The food product can be packaged, packaged under vacuum or packaged at modified atmosphere.

The term "shelf life" means the period of time that a food product remains saleable to retail customers. In traditional meat processing, the shelf life of meat and meat by-products is about 30 to 40 days after an animal has been slaughtered. Refrigeration of meat during this period of time is expected to largely arrest and/or retard the growth of pathogenic bacteria, and to a lesser extent, spoilage bacteria. After about 30 to 40 days, however, refrigeration is no longer able to effectively control the proliferation of spoilage bacteria below acceptable levels.

The term "spoilage bacteria" as used herein refers to any type of bacteria that act to spoil food. Spoilage bacteria may grow and proliferate to such a degree that a food product is made unsuitable or undesirable for human or animal consumption. Bacteria are able to proliferate on food surfaces, such as meat surfaces, by assimilating sugars and proteins on such surfaces. By metabolizing these components, spoilage bacteria create by-products including carbon dioxide, methane, nitrogenous compounds, butyric acid, propionic acid, lactic acid, formic acid, sulfur compounds, and other undesired gases and acids. The production of such by-products alter the color of meat surfaces, often turning meat from a red color to a brown, grey or green color. Gaseous by-products generated by spoilage bacteria also give spoiled meat an undesirable odor. The color and odor alterations of meat due to the growth of spoilage bacteria on a surface of a meat product often make such food product unsaleable to consumers.

In addition to the control of spoilage bacteria, another significant concern in the food processing industry is controlling the growth of food-borne pathogenic bacteria. As used herein, the term "food-borne pathogenic bacteria" refers to any food poisoning organism that is capable of causing disease or illness in animals or humans. The term "pathogenic bacteria" will be understood to include bacteria that infect the food product (for instance meat) and thereby cause disease or illness, as well as bacteria that produce toxins that cause disease or illness. The pathogenic bacteria may be selected from the group: *Aeromonas caviae; Aeromonas hydrophila; Aeromonas sobria; Bacillus cereus; Campylobacter jejuni; Citrobacter* ssp.; *Clostridium botulinum; Clostridium perfringens; Enterobacter* ssp.; *Enterococcus* ssp.; *Escherichia coli* enteroinvasive strains; *Escherichia coli* enteropathogenic strains; *Escherichia coli* enterotoxigenic strains; *Escherichia coli* O157:H7; *Klebsiella* ssp.; *Listeria monocytogenes; Plesiomonas shigelloides; Salmonella* ssp.; *Shigella* ssp.: *Staphylococcus aureus; Streptococcus* ssp.; *Vibrio cholerae; Yersinia enterocolitica*. More preferably, the pathogenic-bacteria are *Listeria monocytogenes.*

The disclosed technology proposes a method to reduce the pathogenic load of *Salmonella* and *Listeria* in pet food products by introducing lactic acid bacteria. Specifically, a strain of *Lactobacillus salivarius* (L28) has been isolated and characterized that effectively reduces *Salmonella* and *Listeria* spp. in a variety of systems, including raw chicken fat and on stainless steel surfaces.

Identification of Lactic Acid Bacteria, Selection and evaluation of lactic acid bacteria as inhibitors of pathogenic bacteria. Can be accomplished by screening environmental cattle fecal samples/retail meat samples for lactic acid bacteria isolates that show antagonisms towards *Salmonella, Escherichia coli* and *Listeria monocytogenes*. The isolation of Lactic Acid Bacteria from samples was performed as follows. The samples were pretreated 10 g+90 ml Physiological water or BPW—stomacher, 2 min. A dilution series ($10^2$-$10^8$) was plated on MRS agar plates. The plates were incubated at 30° C. for 72 hrs. In all cases, the incubation period will need to be extended until visible colonies (white, small and round) appear. Colonies were randomly picked from plates containing 10-100 colonies with similar characteristics and were transferred to MRS broth and incubated 30° C. for 72 hrs. The fermentation MRS broth was streaked on MRS agar plates and incubated at 30° C. for 72 hrs under anaerobic condition to get final purified colonies. These isolates were sub-cultured twice (1% inoculum, 30° C., 24 hrs) in 10 ml MRS broth and kept frozen at −20° C. in MRS supplemented with 10% glycerol. Screening for antimicrobial activity (Agar Well Diffusion Assay). Pathogenic and indicator microorganisms included: *Salmonella* (TSB broth, 30° C., 24 hrs), *E. coli* O157:H7 (TSB broth, 37° C., 18-24 hrs), Non-0157 STECs (TSB broth, 37° C., 18-24 hrs), and *Listeria* (BHI broth, 35° C., 18-24 hrs). The plates were evenly spread with each of indicator bacteria and drops (10 μl) of LAB cultures, growth in MRS broth (37° C., 18-24 hrs). Inhibition was recorded positive if a translucent halo zone was observed around the spot.

Confirming the positive Lactic Acid Bacteria strains. Cultured pathogenic bacteria included: *Salmonella* (TSB broth, 30° C., 24 hrs), *E. coli* O157:H7 (TSB broth, 37° C., 18-24 hrs), Non-O157 STECs (TSB broth, 37° C., 18-24 hrs), and *Listeria* (BHI broth, 35° C., 18-24 hrs). Pathogen and Lactic Acid Bacteria were inoculated into growth media. The samples were kept at refrigerated temperature and room temperature. Antimicrobial activity was analyzed and record under different temperatures.

Identification of Lactic Acid Bacteria. The positive Lactic Acid Bacteria strains were identified using the API 50 CH kit and analyzed by APILAB PLUS software (bioMerieux).

FIG. 1 shows the Lactic Acid Bacteria colony morphology on MRS agar: MRS agar results: Typical lactic acid bacteria colony produced by L28 is shown.

Figure 2:
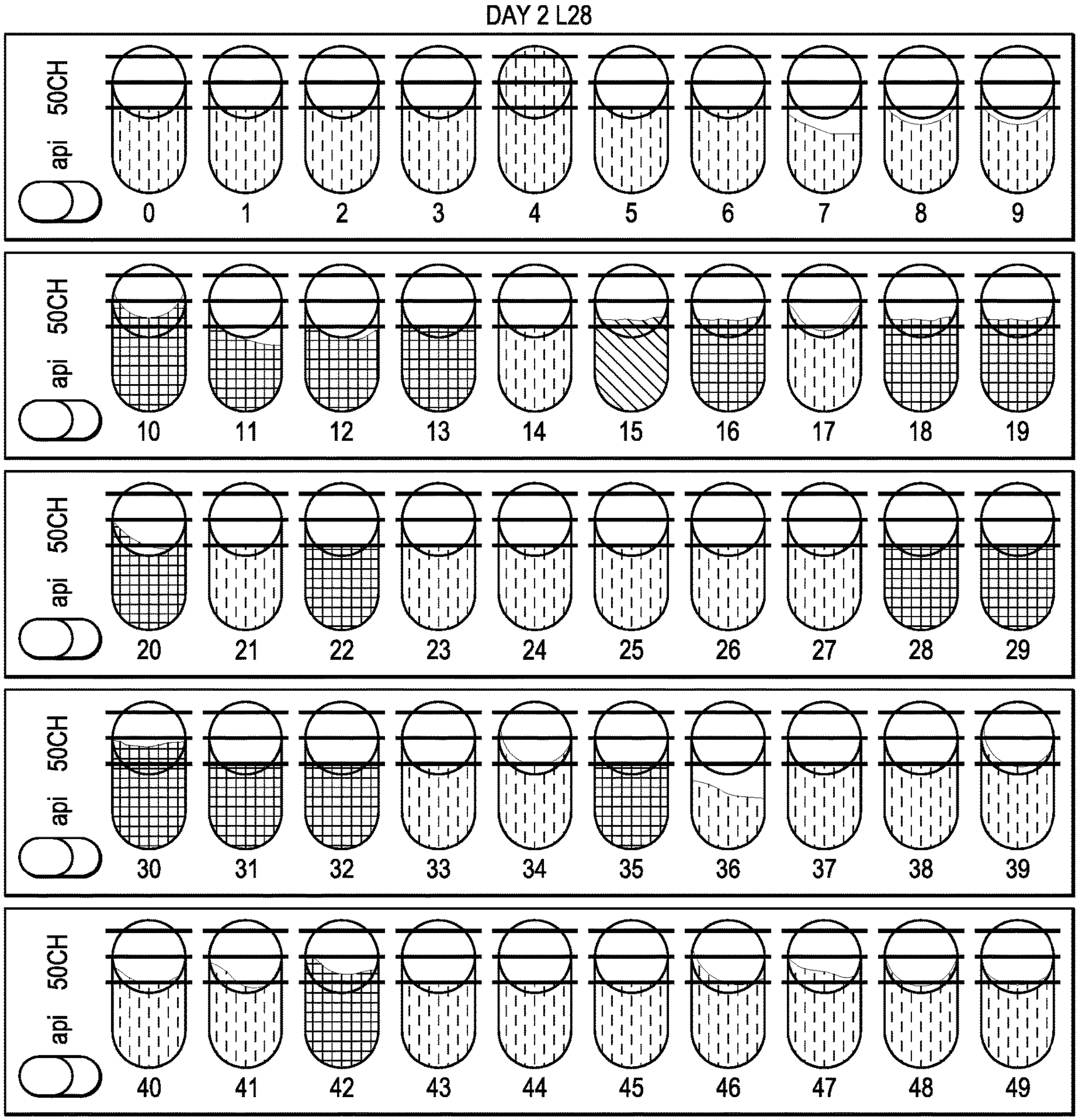
FIG. 2 is an image of the API Strip results L28 Fermentation.

FIG. 2 is an image of the API Strip results L28 Fermentation of following substrates: Wells: 10, 11, 12, 13, 15, 16, 18, 19, 22, 28, 29, 30, 31, 32, 35, and 42.

Figure 3A:
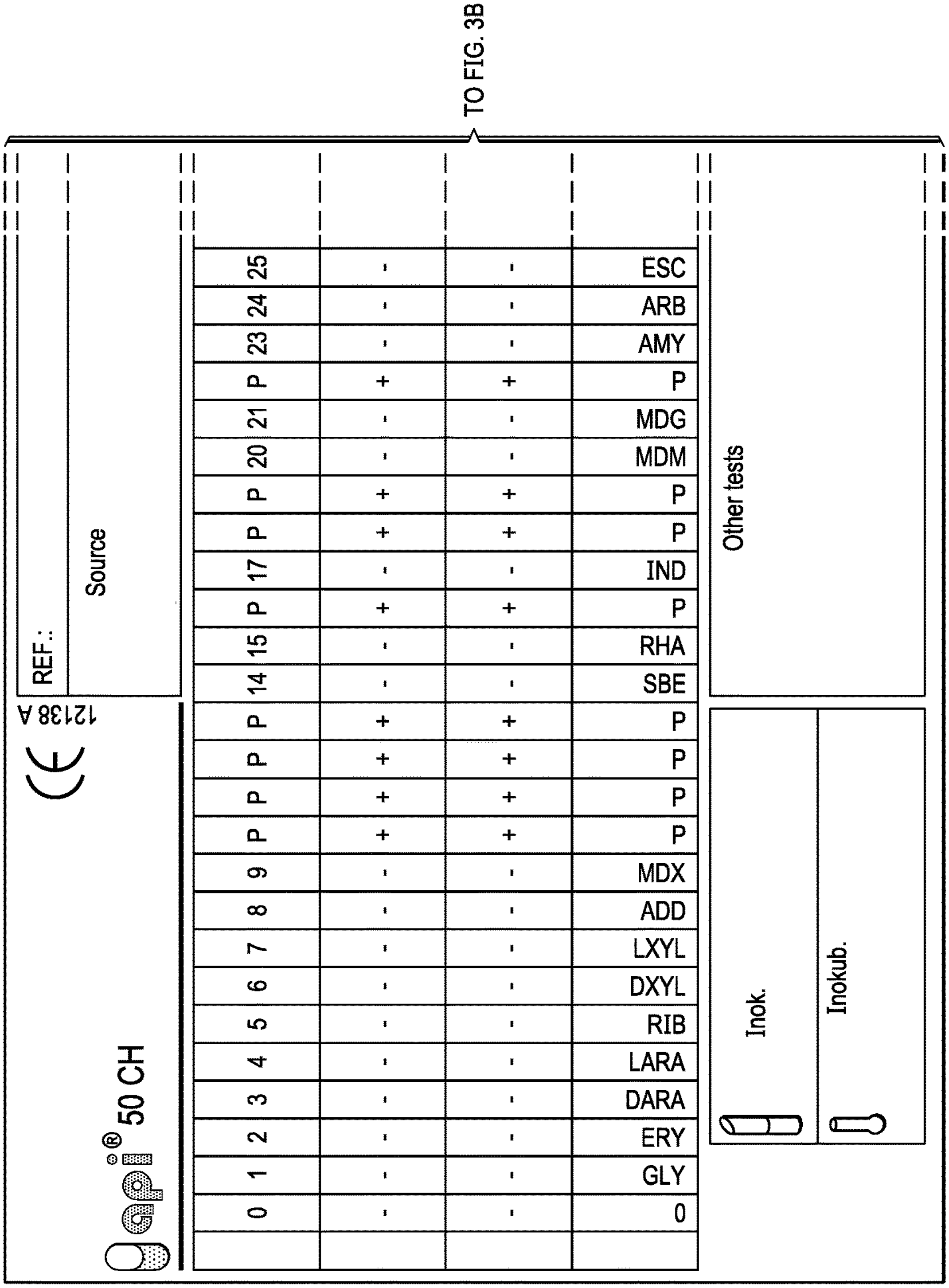
FIG. 3 is an image of the API web software results.
Figure 3B:
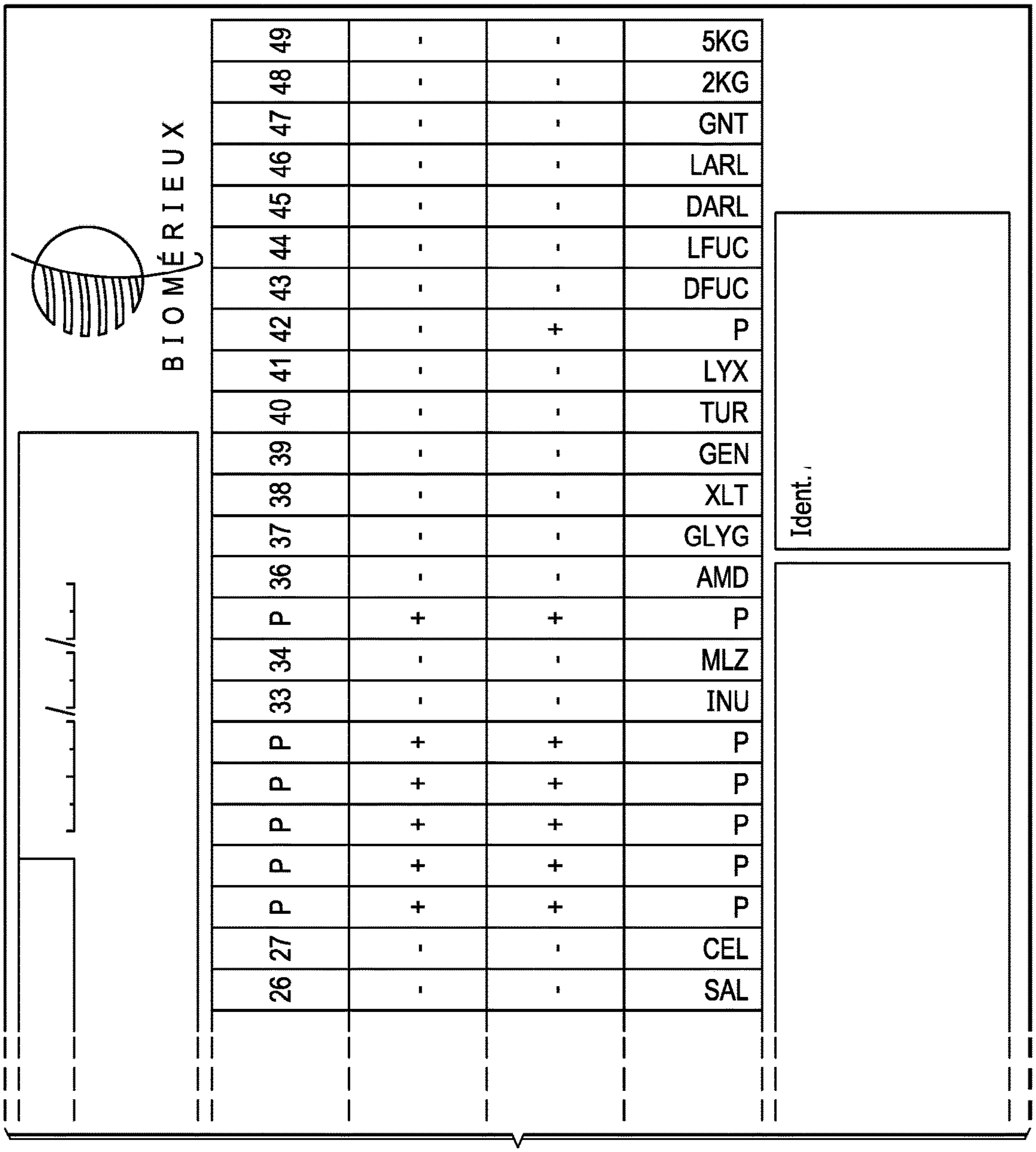

FIG. 3 is an image of the API web software results. Concludes that based on substrates above that it is *Lactobacillus salivarius.*

Figure 4:
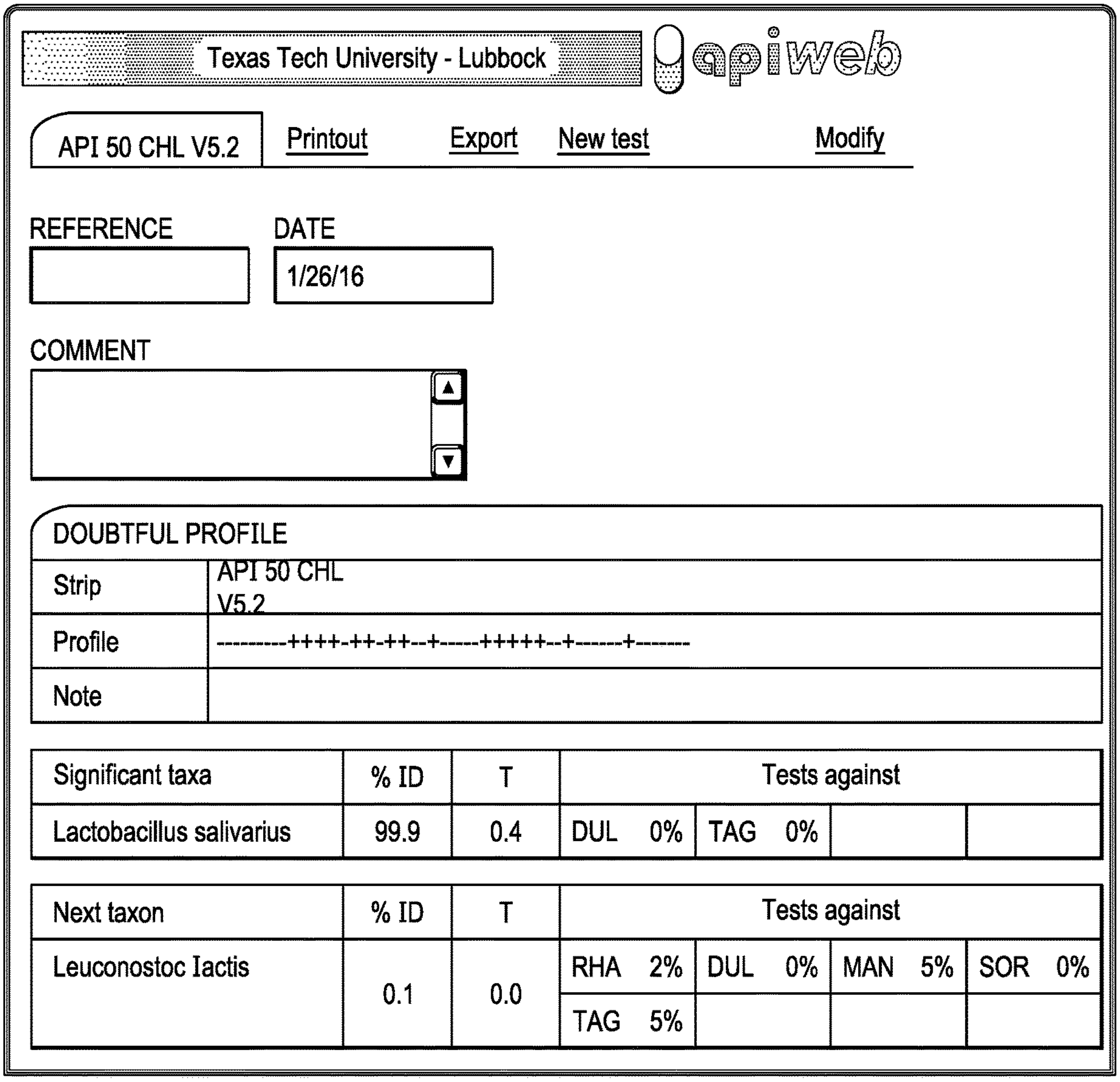
FIG. 4 is an image of a spot agar test plate.

FIG. 4 is an image of a spot agar test plate. Out of hundreds of isolates screened for antimicrobial antagonism towards *Salmonella*, the L28 isolate showed the greatest zone of inhibition. However, the zone of inhibition did depend on the *salmonella* strain. Although, on average the 128 created a zone of inhibition that was approximately a 10 mm zone.

The present invention shows a reduction of *Salmonella* on dry kibble pet food using lactic acid bacteria L28. A collection of Lactic Acid Bacteria isolated from various food sources have shown great inhibitory activity against *Salmonella* when grown in co-culture conditions in laboratory media. Isolate, denoted here as L28, has led to the greatest reductions of *Salmonella* in vitro. L28 isolates have been shown to reduce the *Listeria monocytogenes* on stainless steel to undetectable levels after 24 hrs. In addition, L28 isolates have been shown to significantly reduce *Salmonella* in raw chicken fat after 24 hrs and brought to undetectable levels after day 3. L28 isolates have been shown to reduce significantly *Salmonella* on dry pet food kibble after 4 hrs and undetectable levels after 3 days.

The present invention has been shown to reduce *Salmonella* on a dog kibble. *Salmonella* cultures were prepared using three separate *Salmonella* (Typimurium, Enteritids, Newport) strains that were grown in Tryptic Soy Broth at 37° C. for 24 hrs. After independent strain enrichment, the strains were combines for a 3 strain cocktail. The cocktail was then aliquot, 1 ml into eppendorf tubes with 100 ml of glycerol. Cocktail culture had a final concentration of approximately $\log_{10}$ 8.00 cfu/ml. The three strain cocktail was stored in an ultra-low −80° C. freezer.

Preparation of a lactic acid bacteria culture. L28 was enriched for 24 hrs in MRS broth at 37° C. for 24 hrs. The culture was then aliquot, 1 ml into eppendorf tubes with 100 ml of glycerol. Culture had a final concentration of approximately $\log_{10}$ 8.00 cfu/ml. The culture was stored in an ultra low −80° C. freezer.

Concentrating lactic acid bacteria culture. Two separate one litter bottles of MRS broth were inoculated with 100 microliters of the frozen L28 culture. These two litters of MRS were enriched for 24 hrs at 37° C. To concentrate the L28 culture, the 4 conical tubes with 40 ml of the enriched L28 were centrifuged. The centrifugation parameters were set at 6000 rpm, 6 minutes at 4° C. The pelleted cells were retained and the supernatant was dumped. This process was repeated until all 2 litters were processed. The pellet was re-suspended in 5 ml of supernatant from the MRS broth. The final product yielded approximately 25 ml of concentrated Lactic Acid Bacteria culture at approximately $\log_{10}$ 10.00 cfu/ml.

Inoculation of chicken fat. The chicken fat was provided by the commercial dog food company. Both the chicken fat control group and treatment group got 1 ml of the frozen *Salmonella* cocktail culture ($\log_{10}$ 8.00 cfu/ml) added to 40 ml of chicken fat. The control chicken fat was co-inoculated with a 20 ml cell free/blank of MRS broth. The treatment chicken fat was co-inoculated with a 20 ml $\log_{10}$ 10.00 cfu/ml L28 culture. Thus, a final volume was 60 ml of chicken fat slurry that would be applied to dry dog food kibble.

Application on kibble. For both control group and treatment group ½ (212 grams) pound of dog food was weighed out. The 60 ml of respective chicken fat slurry was added to control and treatment. The initial concentration of *Salmonella* on the dry kibble at zero hour was approximately $\log_{10}$ 6.00 cfu/g. The dry kibble was given 4 hrs to dry under the hood and absorb the chicken fat slurry and facilitate attachment of *salmonella* to the dry kibble.

Figure 5:
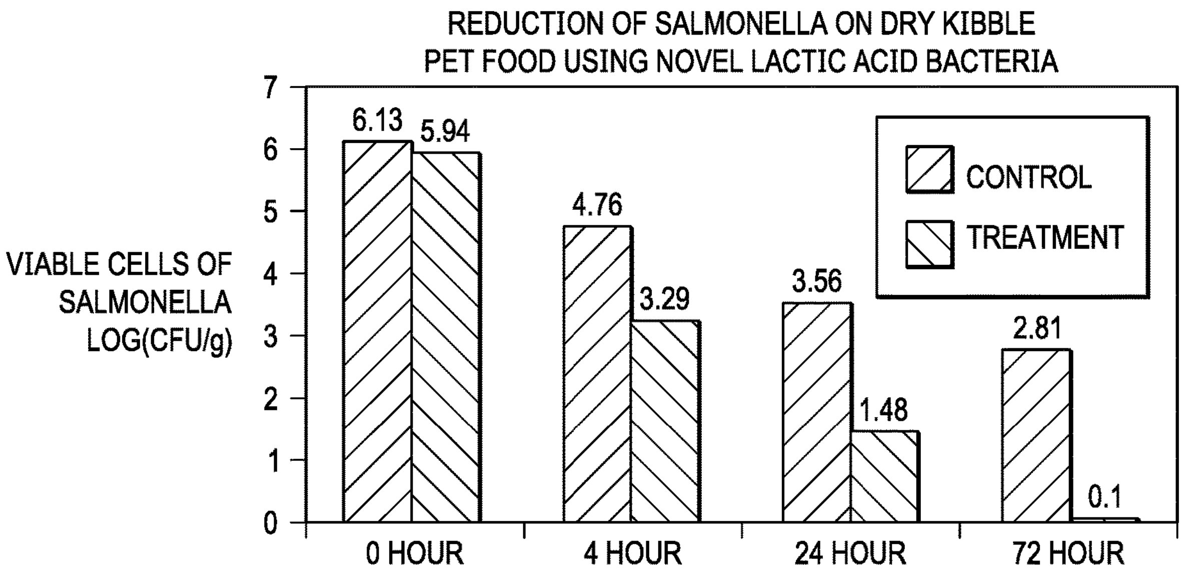
FIG. 5 shows a plot of the reduction of *Salmonella* on dry kibble pet food using novel lactic acid bacteria.

FIG. 5 shows a plot of the Reduction of *Salmonella* on Dry Kibble Pet Food using Novel Lactic Acid Bacteria. After 4 hrs of drying the *Salmonella* on the pet kibble drastically decreased in both the control and treatment groups. However, there was a much bigger decrease of *Salmonella* for treatment group that utilized the L28 Lactic Acid Bacteria intervention. The early reduction at 4 hrs may be due to the production of lactic acid. The culture is concentrated down and instead of re-suspending pellet in buffered peptone water it is re-suspended in its own supernatant. Thus, the method of application of L28 on kibble for these types of reductions in *Salmonella* may affect activity. In comparison of the control and the treatment showed approximately the same log concentration at 0 hrs; approximately 1.5 log reduction at 4 hrs; approximately 2.0 log reduction at 24 hrs; approximately 2.81 log reduction at 72 hrs. *Salmonella* not detected on treatment samples.

The present invention provides novel lactic acid bacteria (L14 and L28) as a biocontrol agent for inhibition of *Salmonella* in a raw chicken fat dog food ingredient. Chicken fat being a rich energy source has many important functions in the canine and feline diet. *Salmonella* is a major pathogen in poultry products and is a frequent carrier of these bacteria.

Figure 6:
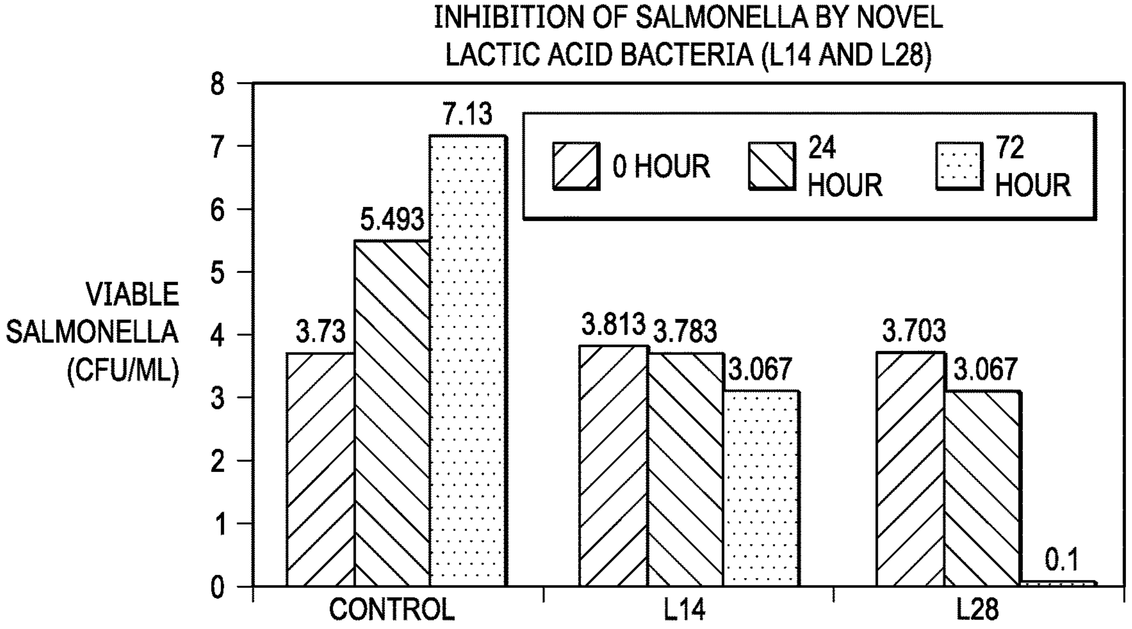
FIG. 6 is an image of the inhibition of *Salmonella* by lactic acid bacteria (L14, L28).

FIG. 6 is an image of the inhibition of *Salmonella* by lactic acid bacteria (L14, L28). The present invention provides novel isolated lactic acid bacteria (LAB)(L14, L28) that reduce the amount of *Salmonella* (*typhimurium*, enteritdis and newport) in raw chicken fat stored at room temperature. Chicken fat was provided by commercial dog food company. For both control and treatment groups, approximately 40 ml of chicken fat was inoculated with a 3-strain *salmonella* for a final concentration of log 3.00 cfu/ml. Each treatment group got respective treatment of (L14 or L28) for a final concentration of log 6.00 cfu/ml. The 40 ml chicken fat was aliquot by 10 ml for each time point, and enumerated on day 0, 1 and 3 on Xylose Lysine deoxycholate (XLD) agar. After day 1 there were statistical significant differences between the control and the treatments for counts of *Salmonella*. By day 1 and 3 the *salmonella* in the control chicken fat had grown to approximately log 5.49 cfu/ml and log 7.13 cfu/ml, respectively. For the L14 treatment on day 3, there was a 4.06 log reduction of *Salmonella*. Moreover, on day 3 for L28 treatment there was a 7.13 log reduction and not detectable by means of direct agar plating method.

Pets that consume contaminated pet kibble can be colonized with *Salmonella* organisms without exhibiting clinical signs, making the pet a possible source of contamination to people in the household. Lactic Acid Bacteria can inhibit *Salmonella* and can be provided to processors in various forms (e.g., frozen, liquid or freeze-dried) and application can be easily implemented into current operations.

The present invention also provides Lactic Acid Bacteria (L28, FS56) as bio-sanitizers to inhibit *Listeria monocytogenes* on stainless steel surfaces. *Listeria monocytogenes* is known to have the ability to attach and form biofilms on many surfaces including stainless steel. Biofilm is not easily removed with common chemical sanitizing methods used in the industry. Therefore, finding innovative ways to inhibit *Listeria monocytogenes* growth and biofilm formation is necessary. The present invention provides Lactic Acid Bacteria (L28) and commercially available (FS56) Lactic Acid Bacteria in inhibition of *Listeria monocytogenes* (N1-002) on stainless steel coupons.

Sterile stainless steel coupons (2 cm×2 cm) were placed into 6-well plates with 2 ml of *Listeria monocytogenes* ($\log_{10}$ 5.00 cfu/ml) and incubated 24 hrs for attachment. After the 24 hrs the *Listeria monocytogenes* was removed and each treatment and control were added. The treatments were with strains L28, FS56 at a concentration of $\log_{10}$ 8.00 cfu/ml and the control was with a blank of de Man, Rogosa and Sharpe (MRS) Broth. The *Listeria monocytogenes* counts were evaluated on modified oxford agar.

Statistical differences (P<0.05) among all of the treatments and the control for counts of *Listeria monocytogenes* were observed. By the end of the 24 hrs the MRS control had increased to log 5.76 cfu/cm$^2$ of *Listeria monocytogenes*. For the treatments, FS56 and L28 had log reduction of 3.1 cfu/cm$^2$ and 5.76 cfu/cm$^2$ respectively. The L28 Lactic Acid Bacteria was so effective that the *Listeria monocytogenes* was not detectable by means of direct agar plating method indicating it is more effective than the FS56 which is currently commercially available.

Animal feed compositions effective in poultry, swine, dogs, sheep, goats, and cattle are generally prepared by mixing the compounds of the present invention with a sufficient amount of animal feed to provide from about 1 to 1000 ppm of the compound in the feed. Animal feed supplements can be prepared by admixing about 75% to 95% by weight of a compound of the present invention with about 5% to about 25% by weight of a suitable carrier or diluent. Carriers suitable for use to make up the feed supplement compositions include the following: alfalfa meal, soybean meal, cottonseed oil meal, linseed oil meal, sodium chloride, cornmeal, cane molasses, urea, bone meal, corncob meal and the like. The carrier promotes a uniform distribution of the active ingredients in the finished feed into which the supplement is blended. It thus performs an important function by ensuring proper distribution of the active ingredient throughout the feed. The supplement is used as a top dressing for the feed, it likewise helps to ensure uniformity of distribution of the active material across the top of the dressed feed.

The preferred medicated swine, dogs, cattle, sheep and goat feed generally contain from 0.01 to 400 grams of active ingredient per ton of feed, the optimum amount for these animals usually being about 50 to 300 grams per ton of feed. The preferred poultry and domestic pet feed usually contain about 0.01 to 400 grams and preferably 10 to 400 grams of active ingredient per ton of feed.

Paste formulations can be prepared by dispersing the active compounds in a pharmaceutically acceptable oil such as peanut oil, sesame oil, corn oil or the like. Pellets containing an effective amount of the compounds of the present invention can be prepared by admixing the compounds of the present invention with a diluent such as carbowax, carnuba wax, and the like, and a lubricant, such as magnesium or calcium stearate, can be added to improve the pelleting process. It is, of course, recognized that more than one pellet may be administered to an animal to achieve the desired dose level which will provide the increase in lean meat deposition and improvement in lean meat to fat ratio desired. Moreover, it has been found that implants may also be made periodically during the animal treatment period in order to maintain the proper drug level in the animal's body. For the poultry and swine raisers, using the method of the present invention yields leaner animals.

TABLE 1 includes numerous strains that can be used with the present invention for a variety of feed, e.g., dog and cat food.

| Name | Source | Gram stain | API estimate | WGS | Antimicrobial Resistance Genes | Virulence Factor Genes |
|---|---|---|---|---|---|---|
| MM13A | Dog | G+ rods | 96.9% *Leuconstoc lactis* | *Lactobacillus animalis* | lnuC [*Streptococcus agalactiae*] | (groEL) chaperonin GroEL [GroEL (CVF403)] [*Clostridium perfringens* str. 13] (SSU98_1513) phosphopyruvate hydratase [Fibronectin-binding protein (AI215)] [*Streptococcus suis* 98HAH33] |
| MM13B | Dog | G+ Cocci | 69.1% *Lactococcus lactis* | Close to *Enterococcus lactis* | msrC [*Enterococcus faecium*] efmA [*Enterococcus faecium*] adeC [*Enterococcus faecium* DO] AAC(6')-Ii [*Enterococcus faecium*] | (EFAU085_00344) LacI family sugar-binding transcriptional regulator [BopD (CVF615)] [*Enterococcus faecium* Aus0085] (tig/ropA) trigger factor [Trigger factor (CVF149)] [*Streptococcus agalactiae* 2603V/R] (clpE) ATP-dependent protease [ClpE (VF0073)] [*Listeria monocytogenes* EGD-e] (EFAU004_00491) periplasmic solute binding protein [EfaA (CVF610)] [*Enterococcus faecium* Aus0004] (tuf) elongation factor Tu [EF-Tu (CVF587)] [*Mycoplasma gallisepticum* str. R(low)] (rfbA-1) glucose-1-phosphate thymidylyltransferase [Capsule (CVF186)] [*Streptococcus gordonii* str. Challis substr. CH1] (rmlB) DTDP-glucose-4,6-dehydratase, putative [Capsule (CVF186)] [*Streptococcus sanguinis* SK36] (SSU98_1513) phosphopyruvate hydratase [Fibronectin-binding protein (AI215)] [*Streptococcus suis* 98HAH33] |

TABLE 1-continued includes numerous strains that can be used with the present invention for a variety of feed, e.g., dog and cat food.

| Name | Source | Gram stain | API estimate | WGS | Antimicrobial Resistance Genes | Virulence Factor Genes |
|---|---|---|---|---|---|---|
| | | | | | | (plr/gapA) glyceraldehyde-3-phosphate dehydrogenase, type I [Streptococcal plasmin receptor/GAPDH (CVF123)] [*Streptococcus pneumoniae* Hungary19A-6] (uppS) undecaprenyl diphosphate synthase [Capsule (CVF618)] [*Enterococcus faecium* Aus0004] (EFAU085_01747) phosphatidate cytidylyltransferase [Capsule (CVF618)] [*Enterococcus faecium* Aus0085] (sagA) SagA [Fibronectin-binding protein (AI158)] [*Enterococcus faecium* U0317] (sgrA) cell wall anchored protein SgrA [SgrA (VF0540)] [*Enterococcus faecium* DO] (sgrA) cell wall anchored protein SgrA [SgrA (VF0540)] [*Enterococcus faecium* DO] (ACI49667) putative pilus tip protein [PilB-type pili (PGS3) (AI133)] [*Enterococcus faecium* str. E1165] (ACI49666) putative minor pilin subunit [PilB-type pili (PGS3) (AI133)] [*Enterococcus faecium* str. E1165] (pilB) PilB [PilB-type pili (PGS3) (AI133)] [*Enterococcus faecium* str. E1165] (ACI49664) putative pilus-dedicated sortase [PilB-type pili (PGS3) (AI133)] [*Enterococcus faecium* str. E1165] (acm) collagen adhesin precursor Acm [Acm (VF0419)] [*Enterococcus faecium* str. TX2555] (M7W_2305) Collagen binding protein Cna [Acm (CVF817)] [*Enterococcus faecium* NRRL B-2354] (M7W_2305) Collagen binding protein Cna [Acm (CVF817)] [*Enterococcus faecium* NRRL B-2354] (bsh) putative conjugated bile acid hydrolase [Bile-salt hydrolase (CVF250)] [*Listeria ivanovii* subsp. *ivanovii* PAM 55] |
| P13 | Dog | | 99.6% *Leuconostoc mesenteroides* | *Weisella paramesenteroides* | | (EFD32_2101) phosphatidate cytidylyltransferase [Capsule (CVF618)] [*Enterococcus faecalis* D32] (tuf) Elongation factor Tu [EF-Tu (CVF587)] [*Mycoplasma synoviae* 53] |
| P17 | Dog | | 91.8% *Lactococcus lactis* | *Enterococcus faecium* | msrC [*Enterococcus faecium*] adeC [*Enterococcus faecium* DO] efmA [*Enterococcus faecium*] tetM [Clostridium difficile 630] AAC(6')-Ii | (plr/gapA) glyceraldehyde-3-phosphate dehydrogenase, type I [Streptococcal plasmin receptor/GAPDH (CVF123)] [*Streptococcus pneumoniae* Hungary 19A-6] (SSU98_1513) phosphopyruvate hydratase [Fibronectin-binding protein (AI215)] [*Streptococcus suis* 98HAH33] (sagA) SagA [Fibronectin-binding protein (AI158)] |

TABLE 1-continued includes numerous strains that can be used with the present invention for a variety of feed, e.g., dog and cat food.

| Name | Source | Gram stain | API estimate | WGS | Antimicrobial Resistance Genes | Virulence Factor Genes |
|---|---|---|---|---|---|---|
| | | | | | [*Enterococcus faecium*] | [*Enterococcus faecium* U0317] (tuf) elongation factor Tu [EF-Tu (CVF587)] [*Mycoplasma gallisepticum* str. R(low)] (tig/ropA) trigger factor [Trigger factor (CVF149)] [*Streptococcus agalactiae* 2603V/R] (rfbA-1) glucose-1-phosphate thymidylyltransferase [Capsule (CVF186)] [*Streptococcus gordonii* str. Challis substr. CH1] (clpE) ATP-dependent protease [ClpE (VF0073)] [*Listeria monocytogenes* EGD-e] (scm) collagen-binding MSCRAMM Scm (Fms10) [Scm (CVF818)] [*Enterococcus faecium* DO] (lisR) two-component response regulator [LisR/LisK (CVF253)] [*Listeria innocua* Clip1 1262] (EFAU08_00344) LacI family sugar-binding transcriptional regulator [BopD (CVF615)] [*Enterococcus faecium* Aus0085] (EFAU085_01747) phosphatidate cytidylyltransferase [Capsule (CVF618)] [*Enterococcus faecium* Aus0085] (uppS) undecaprenyl diphosphate synthase [Capsule (CVF618)] [*Enterococcus faecium* Aus0085] (bsh) putative conjugated bile acid hydrolase [Bile-salt hydrolase (CVF250)] [*Listeria ivanovii* subsp. *ivanovii* PAM 55] (EFAU004_00491) periplasmic solute binding protein [EfaA (CVF610)] [*Enterococcus faecium* Aus0004] (ACI49667) putative pilus tip protein [PilB-type pili (PGS3) (AI133)] [*Enterococcus faecium* str. E1165] (ACI49666) putative minor pilin subunit [PilB-type pili (PGS3) (AI133)] [*Enterococcus faecium* str. E1165] (pilB) PilB [PilB-type pili (PGS3) (AI133)] [*Enterococcus faecium* str. E1165] (ACI49664) putative pilus-dedicated sortase [PilB-type pili (PGS3) (AI133)] [*Enterococcus faecium* str. E1165] (pilF) minor pilin subunit [PilA-type pili (PGS1, pilin gene clusters 1) (AI132)] [*Enterococcus faecium* str. E1165] (ACI49669) hypothetical hydrophobic peptide [PilA-type pili (PGS1, pilin gene clusters 1) (AI132)] [*Enterococcus faecium* str. E1165] (pilE) cell wall-associated LPXTG-like protein [PilA-type pili (PGS1, pilin gene clusters 1) (AI132)] [*Enterococcus faecium* str. E1165] |

TABLE 1-continued includes numerous strains that can be used with the present invention for a variety of feed, e.g., dog and cat food.

| Name | Source | Gram stain | API estimate | WGS | Antimicrobial Resistance Genes | Virulence Factor Genes |
|---|---|---|---|---|---|---|
| | | | | | | (ACI49670) putative pilus-dedicated sortase [PilA-type pili (PGS1, pilin gene clusters 1) (AI132)] [*Enterococcus faecium* str. E1165] (pilA) PilA [PilA-type pili (PGS1, pilin gene clusters 1) (AI132)] [*Enterococcus faecium* str. E1165] (ACI49672) putative housekeeping sortase [PilA-type pili (PGS1, pilin gene clusters 1) (AI132)] [*Enterococcus faecium* str. E1165] (M7W__2305) Collagen binding protein Cna [Acm (CVF817)] [*Enterococcus faecium* NRRL B-2354] (SGO__2024) Extracellular polysaccharide biosynthesis [Capsule (CVF186)] [*Streptococcus gordonii* str. Challis substr. CH1] (bsh) putative conjugated bile acid hydrolase [Bile-salt hydrolase (CVF250)] [*Listeria ivanovii* subsp. *ivanovii* PAM 55] |
| Ecat | Cat | | 64.3% *lactococcus lactis* | *Enterococcus hirae* | AAC(6')-Iid [*Enterococcus hirae*] tetL [*Geobacillus stearothermophilus*] tetM [Clostridium difficile 630] | (lap) bifunctional aldehyde-alcohol dehydrogenase [*Listeria* adhesion protein (CVF228)] [*Listeria monocytogenes* SLCC2755] (capD) capsular polysaccharide synthesis enzyme [Capsule (CVF110)] [*Staphylococcus aureus* subsp. *aureus* MRSA252] (EFD32__2606) polysaccharide lyase family protein [Hyaluronidase (CVF614)] [*Enterococcus faecalis* D32] (tuf) elongation factor Tu [EF-Tu (CVF587)] [*Mycoplasma hyopneumoniae* J] (M3Q__285) nucleoside-diphosphate sugar epimerase [Capsule (CVF775)] [*Acinetobacter baumannii* TYTH-1] (groEL) chaperonin GroEL [GroEL (CVF403)] [*Clostridium beijerinckii* NCIMB 8052] (tuf) elongation factor Tu [Fibronectin-binding protein (AI171)] [*Mycoplasma pneumoniae* M129] (sagA) SagA [Fibronectin-binding protein (AI158)] [*Enterococcus faecium* U0317] (plr/gapA) Glyceraldehyde 3-phosphate dehydrogenase, putative [Streptococcal plasmin receptor/GAPDH (CVF123)] [*Streptococcus sanguinis* SK36] (eno) phosphopyruvate hydratase [Streptococcal enolase (CVF153)] [*Streptococcus pneumoniae* D39] (uppS) undecaprenyl diphosphate synthase [Capsule (CVF618)] [*Enterococcus faecium* Aus0004] |
| J19 | Cabbage | G+ cocci | ? | *Enterococcus faecium* | msrC [*Enterococcus faecium*] | (plr/gapA) glyceraldehyde-3-phosphate dehydrogenase, type I [Streptococcal plasmin |

TABLE 1-continued includes numerous strains that can be used with the present invention for a variety of feed, e.g., dog and cat food.

| Name | Source | Gram stain | API estimate | WGS | Antimicrobial Resistance Genes | Virulence Factor Genes |
|---|---|---|---|---|---|---|
| | | | | | AAC(6')-Ii [*Enterococcus faecium*]<br>efmA [*Enterococcus faecium*]<br>adeC [*Enterococcus faecium* DO] | receptor/GAPDH (CVF123)] [*Streptococcus pneumoniae* Hungary 19A-6]<br>(SSU98_1513) phosphopyruvate hydratase [Fibronectin-binding protein (AI215)] [*Streptococcus suis* 98HAH33]<br>(uppS) undecaprenyl diphosphate synthase [Capsule (CVF618)] [*Enterococcus faecium* Aus0085]<br>(EFAU085_01747) phosphatidate cytidylyltransferase [Capsule (CVF618)] [*Enterococcus faecium* Aus0085]<br>(tig/ropA) trigger factor [Trigger factor (CVF149)] [*Streptococcus agalactiae* 2603V/R]<br>(sagA) SagA [Fibronectin-binding protein (AI158)] [*Enterococcus faecium* U0317]<br>(scm) collagen-binding MSCRAMM Scm (Fms10) [Scm (CVF818)] [*Enterococcus faecium* DO]<br>(scm) collagen-binding MSCRAMM Scm (Fms10) [Scm (CVF818)] [*Enterococcus faecium* DO]<br>(clpE) ATP-dependent protease [ClpE (VF0073)] [*Listeria monocytogenes* EGD-e]<br>(EFAU085_00344) LacI family sugar-binding transcriptional regulator [BopD (CVF615)] [*Enterococcus faecium* Aus0085]<br>(lisR) two-component response regulator [LisR/LisK (CVF253)] [*Listeria innocua* Clip1 1262]<br>(ACI49672) putative housekeeping sortase [PilA-type pili (PGS1, pilin gene clusters 1) (AI132)] [*Enterococcus faecium* str. E1165]<br>(pilA) PilA [PilA-type pili (PGS1, pilin gene clusters 1) (AI132)] [*Enterococcus faecium* str. E1165]<br>(ACI49670) putative pilus-dedicated sortase [PilA-type pili (PGS1, pilin gene clusters 1) (AI132)] [*Enterococcus faecium* str. E1165]<br>(pilE) cell wall-associated LPXTG-like protein [PilA-type pili (PGS1, pilin gene clusters 1) (AI132)] [*Enterococcus faecium* str. E1165]<br>(ACI49669) hypothetical hydrophobic peptide [PilA-type pili (PGS1, pilin gene clusters 1) (AI132)] [*Enterococcus faecium* str. E1165]<br>(pilF) minor pilin subunit [PilA-type pili (PGS1, pilin gene clusters 1) (AI132)] [*Enterococcus faecium* str. E1165]<br>(tuf) elongation factor Tu [EF-Tu (CVF587)] [*Mycoplasma gallisepticum* str. R(low)]<br>(sgrA) cell wall anchored protein SgrA [SgrA (VF0540)] |

TABLE 1-continued includes numerous strains that can be used with the present invention for a variety of feed, e.g., dog and cat food.

| Name | Source | Gram stain | API estimate | WGS | Antimicrobial Resistance Genes | Virulence Factor Genes |
|---|---|---|---|---|---|---|
| | | | | | | [*Enterococcus faecium* DO] (EFAU004_00491) periplasmic solute binding protein [EfaA (CVF610)] [*Enterococcus faecium* Aus0004] (bsh) putative conjugated bile acid hydrolase [Bile-salt hydrolase (CVF250)] [*Listeria ivanovii* subsp. *ivanovii* PAM 55] (rfbA-1) glucose-1-phosphate thymidylyltransferase [Capsule (CVF186)] [*Streptococcus gordonii* str. Challis substr. CH1] (ACI49664) putative pilus-dedicated sortase [PilB-type pili (PGS3) (AI133)] [*Enterococcus faecium* str. E1165] (pilB) PilB [PilB-type pili (PGS3) (AI133)] [*Enterococcus faecium* str. E1165] (ACI49667) putative pilus tip protein [PilB-type pili (PGS3) (AI133)] [*Enterococcus faecium* str. E1165] (bsh) putative conjugated bile acid hydrolase [Bile-salt hydrolase (CVF250)] [*Listeria ivanovii* subsp. *ivanovii* PAM 55] |
| J27 | Grapes | G+ cocci | ? | *Enterococcus faecium* | msrC [*Enterococcus faecium*] AAC(6')-Ii [*Enterococcus faecium*] efmA [*Enterococcus faecium*] adeC [*Enterococcus faecium* DO] | (plr/gapA) glyceraldehyde-3-phosphate dehydrogenase, type I [Streptococcal plasmin receptor/GAPDH (CVF123)] [*Streptococcus pneumoniae* Hungary 19A-6] (SSU98_1513) phosphopyruvate hydratase [Fibronectin-binding protein (AI215)] [*Streptococcus suis* 98HAH33] (uppS) undecaprenyl diphosphate synthase [Capsule (CVF618)] [*Enterococcus faecium* Aus0085] (EFAU085_01747) phosphatidate cytidylyltransferase [Capsule (CVF618)] [*Enterococcus faecium* Aus0085] (tig/ropA) trigger factor [Trigger factor (CVF149)] [*Streptococcus agalactiae* 2603V/R] (sagA) SagA [Fibronectin-binding protein (AI158)] [*Enterococcus faecium* U0317] (scm) collagen-binding MSCRAMM Scm (Fms10) [Scm (CVF818)] [*Enterococcus faecium* DO] (scm) collagen-binding MSCRAMM Scm (Fms10) [Scm (CVF818)] [*Enterococcus faecium* DO] (clpE) ATP-dependent protease [ClpE (VF0073)] [*Listeria monocytogenes* EGD-e] (ACI49667) putative pilus tip protein [PilB-type pili (PGS3) (AI133)] [*Enterococcus faecium* str. E1165] |

TABLE 1-continued includes numerous strains that can be used with the present invention for a variety of feed, e.g., dog and cat food.

| Name | Source | Gram stain | API estimate | WGS | Antimicrobial Resistance Genes | Virulence Factor Genes |
|---|---|---|---|---|---|---|
| | | | | | | (pilB) PilB [PilB-type pili (PGS3) (AI133)] [*Enterococcus faecium* str. E1165]<br>(ACI49664) putative pilus-dedicated sortase [PilB-type pili (PGS3) (AI133)] [*Enterococcus faecium* str. E1165]<br>(EFAU085__00344) LacI family sugar-binding transcriptional regulator [BopD (CVF615)] [*Enterococcus faecium* Aus0085]<br>(pilF) minor pilin subunit [PilA-type pili (PGS1, pilin gene clusters 1) (AI132)] [*Enterococcus faecium* str. E1165]<br>(ACI49669) hypothetical hydrophobic peptide [PilA-type pili (PGS1, pilin gene clusters 1) (AI132)] [*Enterococcus faecium* str. E1165]<br>(pilE) cell wall-associated LPXTG-like protein [PilA-type pili (PGS1, pilin gene clusters 1) (AI132)] [*Enterococcus faecium* str. E1165]<br>(ACI49670) putative pilus-dedicated sortase [PilA-type pili (PGS1, pilin gene clusters 1) (AI132)] [*Enterococcus faecium* str. E1165]<br>(pilA) PilA [PilA-type pili (PGS1, pilin gene clusters 1) (AI132)] [*Enterococcus faecium* str. E1165]<br>(ACI49672) putative housekeeping sortase [PilA-type pili (PGS1, pilin gene clusters 1) (AI132)] [*Enterococcus faecium* str. E1165]<br>(tuf) elongation factor Tu [EF-Tu (CVF587)] [*Mycoplasma gallisepticum* str. R(low)]<br>(EFAU004__00491) periplasmic solute binding protein [EfaA (CVF610)] [*Enterococcus faecium* Aus0004]<br>(sgrA) cell wall anchored protein SgrA [SgrA (VF0540)] [*Enterococcus faecium* DO]<br>(rfbA-1) glucose-1-phosphate thymidylyltransferase [Capsule (CVF186)] [*Streptococcus gordonii* str. Challis substr. CH1]<br>(bsh) putative conjugated bile acid hydrolase [Bile-salt hydrolase (CVF250)] [*Listeria ivanovii* subsp. *ivanovii* PAM 55]<br>(lisR) two-component response regulator [LisR/LisK (CVF253)] [*Listeria innocua* Clip1 1262] |
| J35 | Tofu | G+ cocci | ? | *Enterococcus faecium* | AAC(6')-Ii [*Enterococcus faecium*]<br>efmA [*Enterococcus faecium*]<br>adeC [*Enterococcus faecium* DO]<br>msrC | (plr/gapA) glyceraldehyde-3-phosphate dehydrogenase, type I [Streptococcal plasmin receptor/GAPDH (CVF123)] [*Streptococcus pneumoniae* Hungary 19A-6]<br>(SSU98__1513) phosphopyruvate hydratase [Fibronectin-binding protein (AI215)] [*Streptococcus suis* 98HAH33] |

TABLE 1-continued includes numerous strains that can be used with the present invention for a variety of feed, e.g., dog and cat food.

| Name | Source | Gram stain | API estimate | WGS | Antimicrobial Resistance Genes | Virulence Factor Genes |
|---|---|---|---|---|---|---|
| | | | | | [*Enterococcus faecium*] | (EFAU085__00344) LacI family sugar-binding transcriptional regulator [BopD (CVF615)] [*Enterococcus faecium* Aus0085]<br>(tuf) elongation factor Tu [EF-Tu (CVF587)] [*Mycoplasma gallisepticum* str. R(low)]<br>(scm) collagen-binding MSCRAMM Scm (Fms10) [Scm (CVF818)] [*Enterococcus faecium* DO]<br>(scm) collagen-binding MSCRAMM Scm (Fms10) [Scm (CVF818)] [*Enterococcus faecium* DO]<br>(clpE) ATP-dependent protease [ClpE (VF0073)] [*Listeria monocytogenes* EGD-e]<br>(sagA) SagA [Fibronectin-binding protein (AI158)] [*Enterococcus faecium* U0317]<br>(pilF) minor pilin subunit [PilA-type pili (PGS1, pilin gene clusters 1) (AI132)] [*Enterococcus faecium* str. E1165]<br>(ACI49669) hypothetical hydrophobic peptide [PilA-type pili (PGS1, pilin gene clusters 1) (AI132)] [*Enterococcus faecium* str. E1165]<br>(pilE) cell wall-associated LPXTG-like protein [PilA-type pili (PGS1, pilin gene clusters 1) (AI132)] [*Enterococcus faecium* str. E1165]<br>(ACI49670) putative pilus-dedicated sortase [PilA-type pili (PGS1, pilin gene clusters 1) (AI132)] [*Enterococcus faecium* str. E1165]<br>(pilA) PilA [PilA-type pili (PGS1, pilin gene clusters 1) (AI132)] [*Enterococcus faecium* str. E1165]<br>(ACI49672) putative housekeeping sortase [PilA-type pili (PGS1, pilin gene clusters 1) (AI132)] [*Enterococcus faecium* str. E1165]<br>(EFAU004__00491) periplasmic solute binding protein [EfaA (CVF610)] [*Enterococcus faecium* Aus0004]<br>(tig/ropA) trigger factor [Trigger factor (CVF149)] [*Streptococcus agalactiae* 2603V/R]<br>(rfbA-1) glucose-1-phosphate thymidylyltransferase [Capsule (CVF186)] [*Streptococcus gordonii* str. Challis substr. CH1]<br>(bsh) putative conjugated bile acid hydrolase [Bile-salt hydrolase (CVF250)] [*Listeria ivanovii* subsp. *ivanovii* PAM 55]<br>(uppS) undecaprenyl diphosphate synthase [Capsule (CVF618)] [*Enterococcus faecium* Aus0085]<br>(EFAU085__01747) phosphatidate cytidylyltransferase [Capsule |

TABLE 1-continued includes numerous strains that can be used with the present invention for a variety of feed, e.g., dog and cat food.

| Name | Source | Gram stain | API estimate | WGS | Antimicrobial Resistance Genes | Virulence Factor Genes |
|---|---|---|---|---|---|---|
| | | | | | | (CVF618)] [*Enterococcus faecium* Aus0085] (ACI49664) putative pilus-dedicated sortase [PilB-type pili (PGS3) (AI133)] [*Enterococcus faecium* str. E1165] (pilB) PilB [PilB-type pili (PGS3) (AI133)] [*Enterococcus faecium* str. E1165] (ACI49667) putative pilus tip protein [PilB-type pili (PGS3) (AI133)] [*Enterococcus faecium* str. E1165] (rmlC) dTDP-4-keto-L-rhamnose reductase [Capsule (CVF186)] [*Streptococcus thermophilus* LMG 18311] (lisR) two-component response regulator [LisR/LisK (CVF253)] [*Listeria innocua* Clip1 1262] (sgrA) cell wall anchored protein SgrA [SgrA (VF0540)] [*Enterococcus faecium* DO] |
| J43 | Carrot | G+ cocci | ? | *Enterococcus faecium* | msrC [*Enterococcus faecium*] AAC(6')-Ii [*Enterococcus faecium*] efmA [*Enterococcus faecium*] adeC [*Enterococcus faecium* DO] | (SSU98_1513) phosphopyruvate hydratase [Fibronectin-binding protein (AI215)] [*Streptococcus suis* 98HAH33] (plr/gapA) glyceraldehyde-3-phosphate dehydrogenase, type I [Streptococcal plasmin receptor/GAPDH (CVF123)] [*Streptococcus pneumoniae* Hungary 19A-6] (ACI49667) putative pilus tip protein [PilB-type pili (PGS3) (AI133)] [*Enterococcus faecium* str. E1165] (pilB) PilB [PilB-type pili (PGS3) (AI133)] [*Enterococcus faecium* str. E1165] (ACI49664) putative pilus-dedicated sortase [PilB-type pili (PGS3) (AI133)] [*Enterococcus faecium* str. E1165] (uppS) undecaprenyl diphosphate synthase [Capsule (CVF618)] [*Enterococcus faecium* Aus0085] (EFAU085_01747) phosphatidate cytidylyltransferase [Capsule (CVF618)] [*Enterococcus faecium* Aus0085] (tig/ropA) trigger factor [Trigger factor (CVF149)] [*Streptococcus agalactiae* 2603V/R] (sagA) SagA [Fibronectin-binding protein (AI158)] [*Enterococcus faecium* U0317] (scm) collagen-binding MSCRAMM Scm (Fms10) [Scm (CVF818)] [*Enterococcus faecium* DO] (scm) collagen-binding MSCRAMM Scm (Fms10) [Scm (CVF818)] [*Enterococcus faecium* DO] (clpE) ATP-dependent protease [ClpE (VF0073)] [*Listeria monocytogenes* EGD-e] (EFAU085_00344) LacI family sugar-binding transcriptional regulator [BopD (CVF615)] [*Enterococcus faecium* Aus0085] |

TABLE 1-continued includes numerous strains that can be used with the present invention for a variety of feed, e.g., dog and cat food.

| Name | Source | Gram stain | API estimate | WGS | Antimicrobial Resistance Genes | Virulence Factor Genes |
|---|---|---|---|---|---|---|
| | | | | | | (lisR) two-component response regulator [LisR/LisK (CVF253)] [*Listeria innocua* Clip1 1262] (ACI49672) putative housekeeping sortase [PilA-type pili (PGS1, pilin gene clusters 1) (AI132)] [*Enterococcus faecium* str. E1165] (pilA) PilA [PilA-type pili (PGS1, pilin gene clusters 1) (AI132)] [*Enterococcus faecium* str. E1165] (ACI49670) putative pilus-dedicated sortase [PilA-type pili (PGS1, pilin gene clusters 1) (AI132)] [*Enterococcus faecium* str. E1165] (pilE) cell wall-associated LPXTG-like protein [PilA-type pili (PGS1, pilin gene clusters 1) (AI132)] [*Enterococcus faecium* str. E1165] (ACI49669) hypothetical hydrophobic peptide [PilA-type pili (PGS1, pilin gene clusters 1) (AI132)] [*Enterococcus faecium* str. E1165] (pilF) minor pilin subunit [PilA-type pili (PGS1, pilin gene clusters 1) (AI132)] [*Enterococcus faecium* str. E1165] (tuf) elongation factor Tu [EF-Tu (CVF587)] [*Mycoplasma gallisepticum* str. R(low)] (EFAU004_00491) periplasmic solute binding protein [EfaA (CVF610)] [*Enterococcus faecium* Aus0004] (rfbA-1) glucose-1-phosphate thymidylyltransferase [Capsule (CVF186)] [*Streptococcus gordonii* str. Challis substr. CH1] (bsh) putative conjugated bile acid hydrolase [Bile-salt hydrolase (CVF250)] [*Listeria ivanovii* subsp. *ivanovii* PAM 55] (sgrA) cell wall anchored protein SgrA [SgrA (VF0540)] [*Enterococcus faecium* DO] |
| L14 | Ground Beef | G+ cocci | 84.4% *Lactobacillus acidopholus* | *Enterococcus hirae* | AAC(6')-Iid [*Enterococcus hirae*] | (groEL) chaperonin GroEL [GroEL (CVF403)] [*Clostridium beijerinckii* NCIMB 8052] (tuf) elongation factor Tu [Fibronectin-binding protein (AI171)] [*Mycoplasma pneumoniae* M129] (eno) phosphopyruvate hydratase [Streptococcal enolase (CVF153)] [*Streptococcus pneumoniae* D39] (plr/gapA) Glyceraldehyde 3-phosphate dehydrogenase, putative [Streptococcal plasmin receptor/GAPDH (CVF123)] [*Streptococcus sanguinis* SK36] (capD) capsular polysaccharide synthesis enzyme [Capsule (CVF110)] [*Staphylococcus aureus* subsp. aureus MRSA252] (M3Q_285) nucleoside-diphosphate sugar epimerase [Capsule (CVF775)] |

TABLE 1-continued includes numerous strains that can be used with the present invention for a variety of feed, e.g., dog and cat food.

| Name | Source | Gram stain | API estimate | WGS | Antimicrobial Resistance Genes | Virulence Factor Genes |
|---|---|---|---|---|---|---|
| | | | | | | [*Acinetobacter baumannii* TYTH-1] (tuf) elongation factor Tu [EF-Tu (CVF587)] [*Mycoplasma hyopneumoniae* J] (EFD32_2606) polysaccharide lyase family protein [Hyaluronidase (CVF614)] [*Enterococcus faecalis* D32] (uppS) undecaprenyl diphosphate synthase [Capsule (CVF618)] [*Enterococcus faecium* Aus0004] (ACI49672) putative housekeeping sortase [PilA-type pili (PGS1, pilin gene clusters 1) (AI132)] [*Enterococcus faecium* str. E1165] (pilA) PilA [PilA-type pili (PGS1, pilin gene clusters 1) (AI132)] [*Enterococcus faecium* str. E1165] (ACI49670) putative pilus-dedicated sortase [PilA-type pili (PGS1, pilin gene clusters 1) (AI132)] [*Enterococcus faecium* str. E1165] (pilE) cell wall-associated LPXTG-like protein [PilA-type pili (PGS1, pilin gene clusters 1) (AI132)] [*Enterococcus faecium* str. E1165] (ACI49669) hypothetical hydrophobic peptide [PilA-type pili (PGS1, pilin gene clusters 1) (AI132)] [*Enterococcus faecium* str. E1165] (pilF) minor pilin subunit [PilA-type pili (PGS1, pilin gene clusters 1) (AI132)] [*Enterococcus faecium* str. E1165] (sagA) SagA [Fibronectin-binding protein (AI158)] [*Enterococcus faecium* U0317] (lap) bifunctional aldehyde-alcohol dehydrogenase [*Listeria* adhesion protein (CVF228)] [*Listeria monocytogenes* SLCC2755] (SGO_2024) Extracellular polysaccharide biosynthesis [Capsule (CVF186)] [*Streptococcus gordonii* str. Challis substr. CH1] |
| L15 | Ground Beef | G+ rods | ? | *Lactobacillus sakei* | | (SSU98_1513) phosphopyruvate hydratase [Fibronectin-binding protein (AI215)] [*Streptococcus suis* 98HAH33] (rfbB-1) dTDP-glucose 4,6-dehydratase [Capsule (CVF186)] [*Streptococcus gordonii* str. Challis substr. CH1] |
| L17 | Ground Beef | G+ rods | ? | *Lactobacillus sakei* | | (SSU98_1513) phosphopyruvate hydratase [Fibronectin-binding protein (AI215)] [*Streptococcus suis* 98HAH33] (rfbB-1) dTDP-glucose 4,6-dehydratase [Capsule (CVF186)] [*Streptococcus gordonii* str. Challis substr. CH1] |

TABLE 1-continued includes numerous strains that can be used with the present invention for a variety of feed, e.g., dog and cat food.

| Name | Source | Gram stain | API estimate | WGS | Antimicrobial Resistance Genes | Virulence Factor Genes |
|---|---|---|---|---|---|---|
| L19 | Chicken legs | | ? | *Enterococcus faecium* | msrC [*Enterococcus faecium*] AAC(6')-Ii [*Enterococcus faecium*] adeC [*Enterococcus faecium* DO] efmA [*Enterococcus faecium*] | (plr/gapA) glyceraldehyde-3-phosphate dehydrogenase, type I [Streptococcal plasmin receptor/GAPDH (CVF123)] [*Streptococcus pneumoniae* Hungary 19A-6] (SSU98_1513) phosphopyruvate hydratase [Fibronectin-binding protein (AI215)] [*Streptococcus suis* 98HAH33] (sagA) SagA [Fibronectin-binding protein (AI158)] [*Enterococcus faecium* U0317] (scm) collagen-binding MSCRAMM Scm (Fms10) [Scm (CVF818)] [*Enterococcus faecium* DO] (scm) collagen-binding MSCRAMM Scm (Fms10) [Scm (CVF818)] [*Enterococcus faecium* DO] (clpE) ATP-dependent protease [ClpE (VF0073)] [*Listeria monocytogenes* EGD-e] (EFAU085_00344) LacI family sugar-binding transcriptional regulator [BopD (CVF615)] [*Enterococcus faecium* Aus0085] (uppS) undecaprenyl diphosphate synthase [Capsule (CVF618)] [*Enterococcus faecium* Aus0085] (EFAU085_01747) phosphatidate cytidylyltransferase [Capsule (CVF618)] [*Enterococcus faecium* Aus0085] (tig/ropA) trigger factor [Trigger factor (CVF149)] [*Streptococcus agalactiae* 2603V/R] (lisR) two-component response regulator [LisR/LisK (CVF253)] [*Listeria innocua* Clip1 1262] (ACI49672) putative housekeeping sortase [PilA-type pili (PGS1, pilin gene clusters 1) (AI132)] [*Enterococcus faecium* str. E1165] (pilA) PilA [PilA-type pili (PGS1, pilin gene clusters 1) (AI132)] [*Enterococcus faecium* str. E1165] (ACI49670) putative pilus-dedicated sortase [PilA-type pili (PGS1, pilin gene clusters 1) (AI132)] [*Enterococcus faecium* str. E1165] (pilE) cell wall-associated LPXTG-like protein [PilA-type pili (PGS1, pilin gene clusters 1) (AI132)] [*Enterococcus faecium* str. E1165] (ACI49669) hypothetical hydrophobic peptide [PilA-type pili (PGS1, pilin gene clusters 1) (AI132)] [*Enterococcus faecium* str. E1165] (pilF) minor pilin subunit [PilA-type pili (PGS1, pilin gene clusters 1) (AI132)] [*Enterococcus faecium* str. E1165] |

TABLE 1-continued includes numerous strains that can be used with the present invention for a variety of feed, e.g., dog and cat food.

| Name | Source | Gram stain | API estimate | WGS | Antimicrobial Resistance Genes | Virulence Factor Genes |
|---|---|---|---|---|---|---|
| | | | | | | (tuf) elongation factor Tu [EF-Tu (CVF587)] [*Mycoplasma gallisepticum* str. R(low)]<br>(EFAU004_00491) periplasmic solute binding protein [EfaA (CVF610)] [*Enterococcus faecium* Aus0004]<br>(rfbA-1) glucose-1-phosphate thymidylyltransferase [Capsule (CVF186)] [*Streptococcus gordonii* str. Challis substr. CH1]<br>(bsh) putative conjugated bile acid hydrolase [Bile-salt hydrolase (CVF250)] [*Listeria ivanovii* subsp. *ivanovii* PAM 55]<br>(ACI49664) putative pilus-dedicated sortase [PilB-type pili (PGS3) (AI133)] [*Enterococcus faecium* str. E1165]<br>(pilB) PilB [PilB-type pili (PGS3) (AI133)] [*Enterococcus faecium* str. E1165]<br>(ACI49667) putative pilus tip protein [PilB-type pili (PGS3) (AI133)] [*Enterococcus faecium* str. E1165]<br>(bsh) putative conjugated bile acid hydrolase [Bile-salt hydrolase (CVF250)] [*Listeria ivanovii* subsp. *ivanovii* PAM 55]<br>(sgrA) cell wall anchored protein SgrA [SgrA (VF0540)] [*Enterococcus faecium* DO] |
| LP28 | Ground Beef | G+ rods | 99.9% *Lactobacillus salivarius* | *Lactobacillus salivarius* | tetM [*Clostridium difficile* 630] | (SSU98_1513) phosphopyruvate hydratase [Fibronectin-binding protein (AI215)] [*Streptococcus suis* 98HAH33]<br>(plr/gapA) glyceraldehyde-3-phosphate dehydrogenase [Streptococcal plasmin receptor/GAPDH (CVF123)] [*Streptococcus agalactiae* A909]<br>(groEL) chaperonin GroEL [GroEL (CVF403)] [*Clostridium perfringens* str. 13]<br>(clpC) endopeptidase Clp ATP-binding chain C [ClpC (VF0072)] [*Listeria monocytogenes* EGD-e]<br>(hlyA) putative rRNA methylase [Hemolysin (CVF589)] [*Mycoplasma mobile* 163K]<br>(galU) UTP--glucose-1-phosphate uridylyltransferase [LOS (CVF494)] [*Haemophilus somnus* 129PT]<br>(sspA) surface protein C [Antigen I/II (AgI/II) family of oral streptococcal adhesins (CVF125)] [*Streptococcus sanguinis* SK36]<br>(licD) lipopolysaccharide choline phosphotransferase [LOS (CVF494)] [*Haemophilus somnus* 129PT]<br>(rffG) dTDP-glucose 46-dehydratase [LOS (CVF494)] [*Haemophilus influenzae* PittGG]<br>(rmlA) putative glucose-1-phosphate thymidyltransferase [Capsule (CVF186)] |

TABLE 1-continued includes numerous strains that can be used with the present invention for a variety of feed, e.g., dog and cat food.

| Name | Source | Gram stain | API estimate | WGS | Antimicrobial Resistance Genes | Virulence Factor Genes |
|---|---|---|---|---|---|---|
| | | | | | | [*Streptococcus mutans* UA159] (tuf) elongation factor Tu [EF-Tu (CVF587)] [*Mycoplasma penetrans* HF-2] (tig/ropA) trigger factor [Trigger factor (CVF149)] [*Streptococcus agalactiae* A909] |

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims. All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A method for inhibiting the growth of *Salmonella Typhimurium, Salmonella Enteritidis*, and *Salmonella* Newport serotypes in dog or cat food consisting of:

contacting the dog or cat food with a composition consisting of *Lactobacillus salivarius* L28 (ATCC Deposit No. PTA-127731), in an amount sufficient to reduce or eliminate and *Salmonella* Typimurium, *Salmonella* Enteritids, and *Salmonella* Newport; and incubating the dog or cat food with the *Lactobacillus salivarius* L28 for 72 hours to inhibit the growth of the *Salmonella* Typimurium, *Salmonella* Enteritids, and *Salmonella* Newport in the dog or cat food.

2. The method of claim 1, wherein the *Lactobacillus salivarius* L28 is admixed with the dog or cat food, or coated on the dog or cat food.

3. The method of claim 1, wherein the dog or cat food is a kibble, moist feed, or wet feed.

* * * * *